US00PP22328P2

(12) United States Plant Patent
Katerberg

(10) Patent No.: US PP22,328 P2
(45) Date of Patent: Dec. 13, 2011

(54) *BUXUS* PLANT NAMED 'ESELES'

(50) Latin Name: *Buxus microphylla var. koreana*
Varietal Denomination: Eseles

(75) Inventor: Gerard Katerberg, Muskegon, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 12/807,826

(22) Filed: Sep. 14, 2010

(51) Int. Cl.
*A01H 5/00* (2006.01)

(52) U.S. Cl. ..... Plt./226

(58) Field of Classification Search ..... Plt./226
See application file for complete search history.

*Primary Examiner* — Annette Para
(74) *Attorney, Agent, or Firm* — C. A. Whealy

(57) ABSTRACT

A new and distinct cultivar of *Buxus* plant named 'Eseles', characterized by its compact, mounded and uniform plant habit; freely branching habit; dense and bushy appearance; green and yellow variegated leaves; and good winter hardiness.

2 Drawing Sheets

Botanical designation: *Buxus microphylla* var. *koreana.*
Cultivar denomination: 'ESELES'.

BACKGROUND OF THE INVENTION

The present invention relates to a new and distinct cultivar of *Buxus* plant, commercially produced as an ornamental shrub, botanically known as *Buxus microphylla* var. *koreana* and hereinafter referred to by the name 'Eseles' .

The new *Buxus* plant is a naturally-occurring branch mutation of *Buxus microphylla* var. *koreana* 'Winter Gem', not patented. The new *Buxus* plant was discovered and selected by the Inventor on a single plant of 'Winter Gem' in a controlled outdoor nursery environment in Muskegon, Mich.

Asexual reproduction of the new *Buxus* plant by hardwood cuttings in a controlled environment in Grand Haven, Mich. since December, 1990, has shown that the unique features of this new *Buxus* plant are stable and reproduced true to type in successive generations.

SUMMARY OF THE INVENTION

Plants of the new *Buxus* have not been observed under all possible environmental conditions. The phenotype may vary somewhat with variations in environment such as temperature and light intensity without, however, any variance in genotype.

The following traits have been repeatedly observed and are determined to be the unique characteristics of 'Eseles'. These characteristics in combination distinguish 'Eseles' as a new and distinct cultivar of *Buxus* plant:

1. Compact, mounded and uniform plant habit.
2. Freely branching habit; dense and bushy appearance.
3. Green and yellow variegated leaves.
4. Good winter hardiness.

Plants of the new *Buxus* differ primarily from plants of the mutation parent, 'Winter Gem', in leaf coloration as plants of 'Winter Gem' have solid green-colored leaves.

Plants of the new *Buxus* can be compared to plants of *Buxus microphylla* 'Peergold', disclosed in U.S. Plant Pat. No. 16,052. In side-by-side comparisons conducted in Grand Haven, Mich., plants of the new *Buxus* differed from plants of 'Peergold' in the following characteristics:

1. Plants of the new *Buxus* were more compact than plants of 'Peergold'.
2. Plants of the new *Buxus* were more uniform in plant shape than plants of 'Peergold'.
3. Plants of the new *Buxus* were denser and bushier than and not as open as plants of 'Peergold'.
4. Plants of the new *Buxus* had broader leaves than plants of 'Peergold'.
5. Variegation of leaves of the new *Buxus* was more distinctly contrasting than variegation of leaves of 'Peergold'.
6. Plants of the new *Buxus* were more winter hardy than plants of 'Peergold'.

BRIEF DESCRIPTION OF THE PHOTOGRAPHS

The accompanying colored photographs illustrate the overall appearance of the new *Buxus* plant showing the colors as true as it is reasonably possible to obtain in colored reproductions of this type. Colors in the photographs may differ slightly from the color values cited in the detailed botanical description which accurately describe the colors of the new *Buxus* plant.

The photograph on the first sheet comprises a side perspective view of a typical plant of 'Eseles' grown in an outdoor nursery.

The photograph on the second sheet is a close-up view of a typical plant of 'Eseles'.

DETAILED BOTANICAL DESCRIPTION

The aforementioned photographs and following observations, measurements and values describe plants grown during the summer in an outdoor nursery in Grand Haven, Mich. Plants were two years old when the photographs and description were taken. In the following description, color references are made to The Royal Horticultural Society Colour Chart, 2001 Edition, except where general terms of ordinary dictionary significance are used.

Botanical classification: *Buxus microphylla* var. *koreana* 'Eseles'.

Parentage: Naturally-occurring branch mutation of *Buxus microphylla* var. *koreana* 'Winter Gem', not patented.

Propagation:

*Type.*—By hardwood cuttings.

*Time to initiate roots.*—About one month at 20° C.

*Time to produce a rooted young plant.*—About one year at 25° C.

*Root description.*—Thick and fine; cream in color.

*Rooting habit.*—Freely branching; dense.

Plant description:

*Plant form/habit.*—Evergreen shrub with compact, mounding and uniform plant habit; freely branching habit, about 82 lateral branches developing per plant; dense and bushy appearance; moderately vigorous growth habit.

*Plant height.*—About 50 cm.

*Plant width* (*spread*).—About 50 cm.

*Lateral branches.*—Length: About 12 cm. Diameter: About 2 mm. Internode length: About 1 cm. Strength: Strong. Texture: Smooth, glabrous. Color, developing stems: Close to 144A. Color, developed stems: Close to 199D.

Foliage description:

*Arrangement.*—Opposite, simple.

*Length.*—About 1.5 cm.

*Width.*—About 1 cm.

*Shape.*—Broadly elliptic.

*Apex.*—Rounded.

*Base.*—Obtuse to cuneate.

*Margin.*—Entire.

*Texture, upper and lower surfaces.*—Smooth, glabrous.

*Venation pattern.*—Pinnate.

*Color.*—Developing leaves, upper surface: Center, close to 132A; towards the margins, close to 143B. Developing leaves, lower surface: Close to 143B. Fully expanded leaves, upper surface: Center, close to 132A; towards the margins, close to 8A; venation, similar to leaf surface coloration. Fully expanded leaves, lower surface: Center, close to 143A; towards the margins, close to 150B; venation, similar to surface coloration.

*Petiole.*—Length: About 1 mm. Diameter: About 1.5 mm. Texture, upper and lower surfaces: Smooth, glabrous. Color, upper and lower surfaces: Close to 132A.

Flower description: Flower initiation and development has not been observed on plants of the new *Buxus*.

Disease/pest resistance: Plants of the new *Buxus* have not been noted to be resistant to pathogens and pests common to *Buxus*.

Temperature tolerance: Plants of the new *Buxus* have been observed to tolerate high temperatures of about 30° C. and to be hardy to USDA Hardiness Zone 5.

It is claimed:

1. A new and distinct *Buxus* plant named 'Eseles' as illustrated and described.

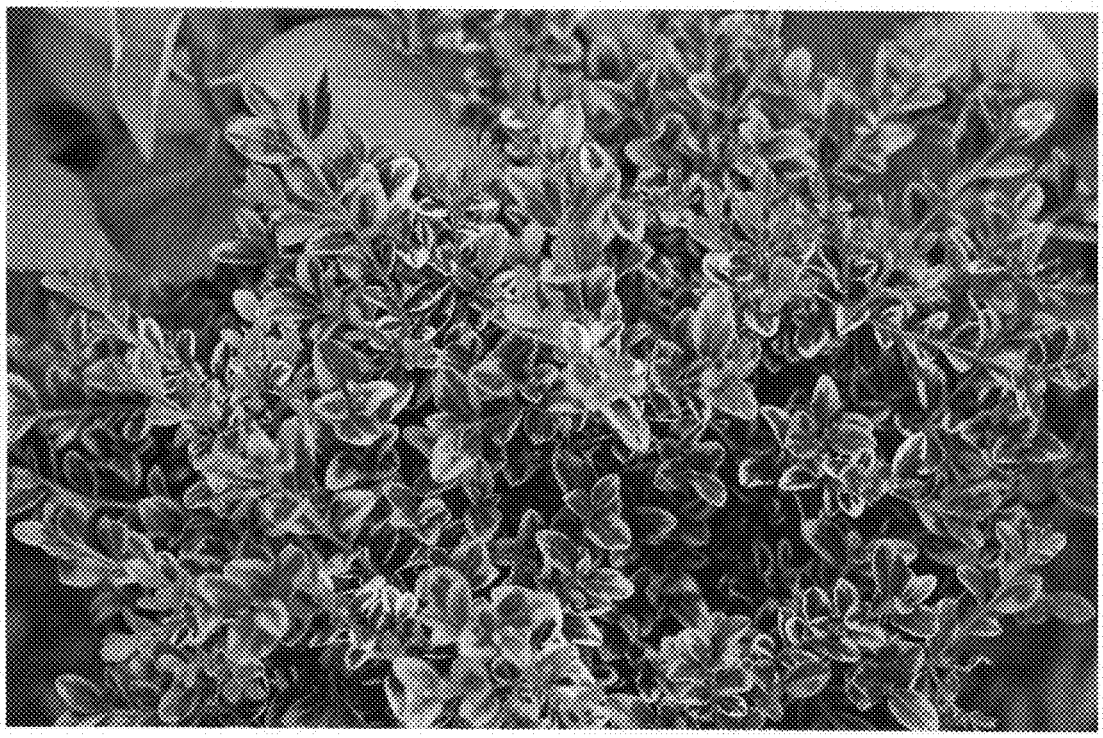

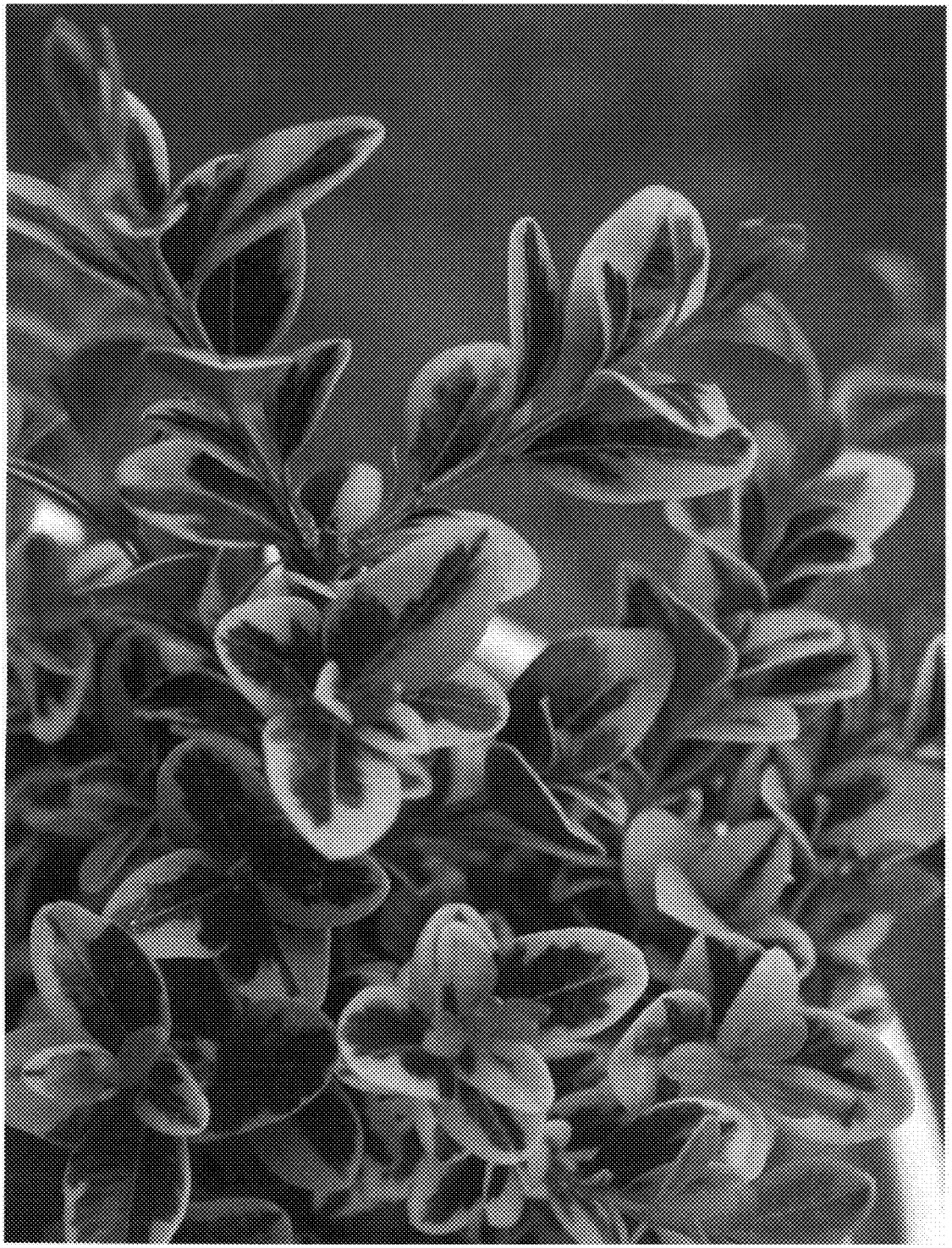

* * * * *